United States Patent
Erdmann et al.

(10) Patent No.: US 6,787,158 B1
(45) Date of Patent: Sep. 7, 2004

(54) PROCESS FOR TREATMENT OF A LACTIC RAW MATERIAL

(75) Inventors: Peter Erdmann, Bern (CH); Fred Neumann, Steffisburg (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/450,217

(22) Filed: Nov. 29, 1999

Related U.S. Application Data

(63) Continuation-in-part of application No. PCT/EP98/03176, filed on May 22, 1998.

(30) Foreign Application Priority Data

May 27, 1997 (EP) .............................. 97201607

(51) Int. Cl.[7] .............................. A61K 35/20
(52) U.S. Cl. ..................... 424/535; 426/41; 426/657; 530/412; 530/416; 530/352
(58) Field of Search ................. 424/535; 426/41, 426/657; 530/412, 416, 352

(56) References Cited

U.S. PATENT DOCUMENTS

| | | | |
|---|---|---|---|
| 5,061,622 A | 10/1991 | Dosako et al. ............. | 435/68.1 |
| 5,063,203 A | 11/1991 | Drouet et al. .................. | 514/8 |
| 5,270,462 A | * 12/1993 | Shimatani .................. | 536/17.2 |
| 5,280,107 A | 1/1994 | Kawasaki et al. .......... | 530/361 |
| 5,434,250 A | * 7/1995 | Shimatani .................. | 530/366 |
| 5,968,586 A | * 10/1999 | Etzel ......................... | 426/657 |

FOREIGN PATENT DOCUMENTS

| | | |
|---|---|---|
| EP | 291264 | 11/1988 |
| GB | 2188526 | 10/1987 |
| WO | 99/18808 * | 4/1999 |

OTHER PUBLICATIONS

McKenzie, Advances in Protein Chemistry 22, 55–66, 1967.*
Yun, K. S., Analytical Chemistry 67(3), 613–19, 1995.*
Scopes (Protein Purification, pp. 68–75, 1982).*
Abstract of JP–05262793, Oct. 12, 1993.*
Abstract of JP–07132049, May 23, 1995.*
Scopes, "Protein Purification" (Springer–Verlag) pp. 75–101, 1982.*
Saito, J. Dairy Sci. 74, 2831–2837, 1991.*
Wolfgang Gerhartz et al., Ullman's Encyclopedia of Industrial Chemistry, 5th Edition, vol. A9, 1987, pp. 416–418.
G.W. Smithers et al.,, New casein protein products for the food industry; Physical, chemical and enzymatic manipulation of milk, *Food Australia*, 1991, 43 (6), 252–254.
S.C. Marshall, Casein Macropeptide From Whey—A New Product Opportunity, *Food Research Quarterly*, 1991, 51, Nos. 1 & 2.
M. Outinen et al., Chromatographic isolation of k–casein macropeptide from cheese whey with a strong basic anion exchange resin, *Caseinomacropeptide*, 1995, 50, 570–574.

* cited by examiner

*Primary Examiner*—Christopher S. F. Low
*Assistant Examiner*—David Lukton
(74) *Attorney, Agent, or Firm*—Winston & Strawn LLP

(57) ABSTRACT

A process is disclosed for extracting glycomacropeptide from a lactic raw material. This process includes the step of treating a lactic raw material containing glycomacropeptide in the presence of a weakly anionic resin wherein the glycomacropeptide is selectively adsorbed onto the resin and then eluted from the resin so as to obtain an improved protein product which can be used in foods, and pharmaceutical and dental compositions.

16 Claims, 1 Drawing Sheet

PROCESS FOR TREATMENT OF A LACTIC RAW MATERIAL

CROSS-REFERENCE TO RELATED APPLICATIONS

This application is a continuation-in-part of copending PCT international application No. PCT/EP98/03176, filed on May 22, 1998.

FIELD OF THE INVENTION

The invention is directed to a process for the separation of glycomacropeptide or caseinoglycomacropeptide ("GMP") from lactic raw material.

BACKGROUND OF THE INVENTION

GMP is a phosphorylated and partially sialylated macropeptide which is formed by the action of a protease, for example rennet, on mammalian milk kappa-casein. GMP represents about 20% by weight of the proteins in sweet whey obtained after separation of casein during cheese manufacture.

A laboratory scale process for the manufacture of GMP is known. The process consists of treating a raw lactic material, such as an acid casein, a caseinate hydrolyzed by rennet, or a demineralized and lactose-free sweet whey from cheesemaking, with trichloroacetic acid so as to precipitate the proteins. The process further consists of recovering the supernatant, dialyzing the supernatant, and drying the separated dialysate. Although known, such a process is not applicable on an industrial scale.

A process for the production of GMP on an industrial scale, which is described in European Patent Application No. 488,589, consists of treating a whey product by ion exchange and recovering the fraction that has not been adsorbed. The process further consists of concentrating the fraction, demineralizing the fraction using ultrafiltration, diafiltration and, if necessary reverse osmosis, and recovering the GMP.

British Patent No. 2,188,526 discloses a process for the production of a whey protein fraction. The process consists of treating a milk product with a strong anionic resin, under conditions such that proteins and some peptides of the treated material are nonselectively adsorbed onto the resin in the form of complexes. These complexes are difficult to subsequently elute from the resin. The eluate forms a firm gel at a pH of less than 4.5 and at room temperature, once the eluate is suspended in water. The protein fraction may be used in drinks of the milk-shake type and in dessert mousses.

Japanese Patent Publication Kokai 07-132049 uses a weakly anionic ion exchange resin whose matrix is hydrophilic to separate the sialylated peptides from whey. The process consists of passing the raw material, whose pH has been beforehand precisely adjusted to a value of 4 to 6, over a hydrophilic macromolecular support consisting of a natural polysaccharide or a synthetic polyvinyl, grafted with basic exchanging groups. The supports used as matrix are not easily applicable industrially.

Despite the aforementioned processes, there is a need for a process which easily and selectively separates a highly purified GMP from lactic raw materials without additional expense and which can be conducted on a large scale. Additionally, it is highly desirable to develop a process that can separate GMP from lactic raw material in a single operation and in high yield.

SUMMARY OF THE INVENTION

The invention relates to a process for the extraction of GMP from a lactic raw material comprising the steps of removing cations from a lactic raw material for a sufficient amount of time to obtain a substantially deionized lactic raw material having a pH of about 1 to 4.5; contacting the substantially deionized lactic raw material with an anionic resin having a hydrophobic matrix for a sufficient amount of time and at a sufficient temperature to remove GMP from the substantially deionized lactic raw material and to obtain a treated liquid material; separating the resin from the treated liquid material; and rinsing the resin to obtain the GMP therefrom.

In this process, the lactic raw material can be one of sweet whey obtained after separation of casein coagulated with rennet, a concentrate of sweet whey, a sweet whey or such a whey demineralized to by electrodialysis, ion exchange, reverse osmosis, electrodeionization or a combination of these procedures, a concentrate of sweet whey demineralized by electrodialysis, ion exchange, reverse osmosis, electrodeionization or a combination of these procedures, a concentrate of proteins of substantially lactose-free sweet whey obtained by ultrafiltration, followed by diafiltration (ultrafiltration with washing), mother liquors of the crystallization of lactose from sweet whey, a permeate of ultrafiltration of a sweet whey, the product of hydrolysis, by a protease, of a native casein obtained by acid precipitation of skimmed milk with an inorganic acid or by biological acidification, where appropriate with addition of calcium ions or alternatively of a micellar casein, obtained by microfiltration of a skimmed milk, the product of hydrolysis of a caseinate by a protease. Preferably, the sweet whey has a solids content of about 10 to 23 percent by weight and is completely deionized during the cation removal step.

Also, the lactic raw material is preferably a liquid or a dispersion of solids in a liquid and calcium ions may be added to the lactic raw material after the cation removal step.

Advantageously, the resin is treated with an alkaline material prior to contact with the substantially deionized lactic raw material. Preferably, the substantially deionized lactic raw material contacts the resin in a gently stirred reactor at a temperature of less than 50° C. for one to ten hours to adsorb the GMP onto the resin. A suitable resin is one that is basic and in macroporous or macrocross-linked gel form. The substantially deionized lactic raw material usually contacts the resin until the treated liquid material attains a constant pH of between about 4.5 to 5.5 to indicate that the reaction has proceeded to completion. Advantageously, the resin and lactic raw material are present in a volume ratio of 1:1 to 1:30.

The invention also relates to the treated liquid material that is obtained from this inventive process. This treated liquid material has an amino acid profile is reduced in threonine and enriched in aromatic amino acids and tryptophan. Relative to the starting lactic raw material, the threonine content is preferably reduced by about 15 to 40%, and the aromatic amino acids and tryptophan are preferably increased by about 20 to 60%. This treated liquid material is useful in an infant or dietetic product as a protein raw material, in a pharmaceutical composition in combination with antithrombotic, antidiarrheal or antibacterial agents, or in a food composition as an emulsifying, gelling or foaming agent. The invention also produces a new GMP which can be used, for example, in a dental composition as an agent against plaque and caries.

DETAILED DESCRIPTION OF THE INVENTION

Figure 1:
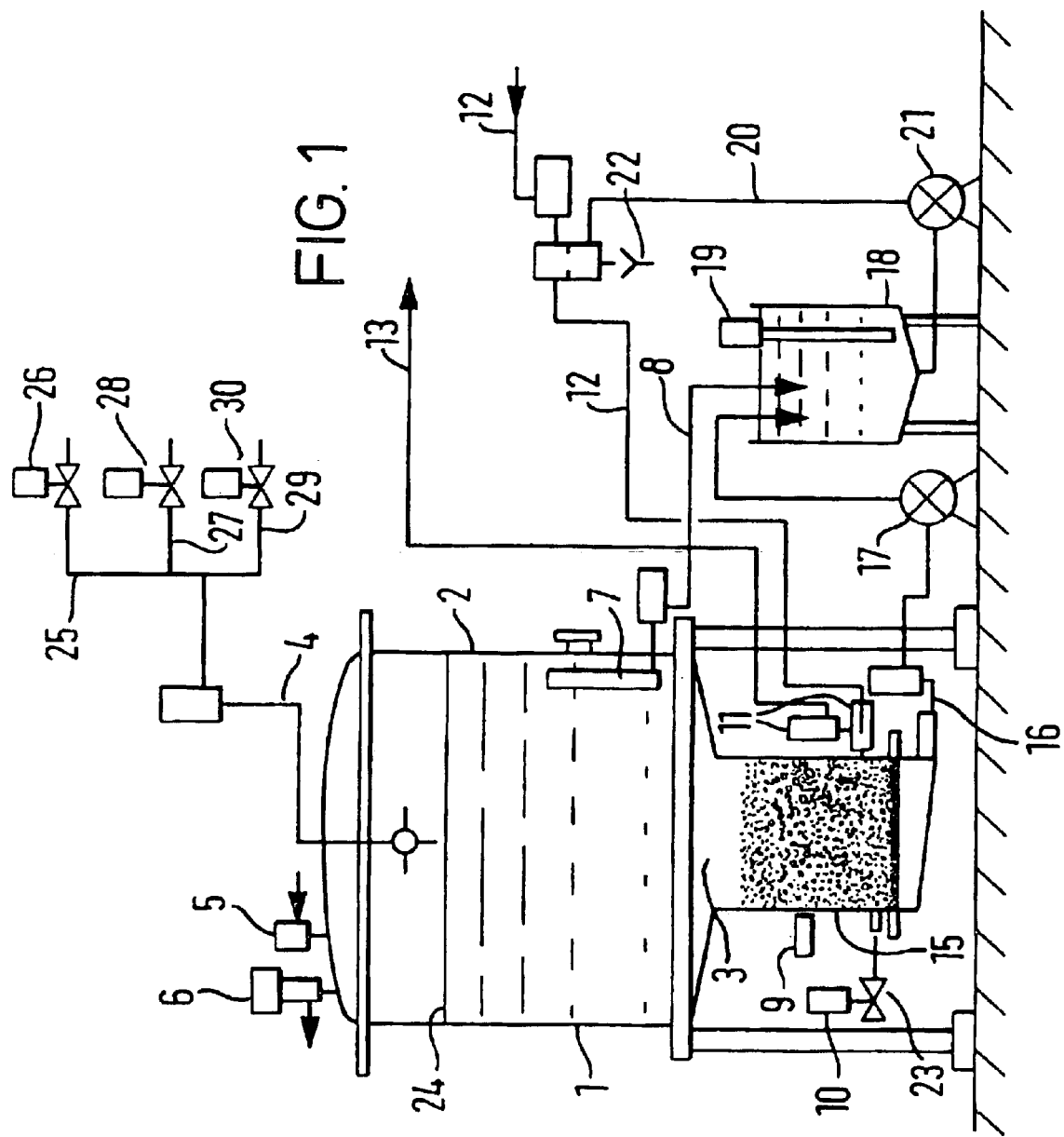
FIG. 1 is a schematic representation of an apparatus capable of separating GMP from lactic raw material.

The present invention is directed to a process for the selective separation of GMP from other components contained within lactic raw materials in a single operation, on an industrial scale, and in high yield. The process of the present invention also is directed to a process for the ion-exchange treatment of a lactic raw material containing GMP, with the aim of recovering a product which can be used directly as protein source or for isolating GMP in a purified form. The powder obtained with the process of the present invention can serve as protein raw material in the preparation of infant products. Moreover, the powder has a very desirable amino acid profile. The powder's aminogram shows a reduction in threonine and an enrichment in aromatic amino acids such as tryptophan.

One embodiment of the process of the present invention comprises the steps of: removing cations from a lactic raw material to obtain a substantially deionized lactic raw material, preferably one having a pH of about 1 to 4.5, contacting the substantially deionized lactic raw material with a weakly anionic resin of hydrophobic matrix, predominantly in alkaline form to obtain a treated liquid material with a stabilized pH, separating the resin from the treated liquid material product, the latter being recovered, and removing the GMP from the resin. The lactic raw material is preferably substantially deionized, prior to GMP extraction. Preferably, in the inventive process, ions such as cations are completely removed, and the term "substantially deionized" is used to indicate almost complete removal, i.e., above 90% cation removal.

Another embodiment of the process, includes the steps of bringing the lactic raw material in liquid form into contact with a weakly anionic resin in a reactor and stirring gently at a temperature of less than 50° C. Preferably, the temperature should be between 0° C. and 15° C. Stirring should be sufficiently vigorous to fluidize the resin bed. The stirring can be produced by a stirrer or preferably by introducing a stream of fluid, such as air or nitrogen, under pressure through the bottom of the reactor.

Yet another embodiment of the process of the present invention, includes the steps of percolating the lactic raw material in liquid form through a column filled with the resin, collecting the treated liquid material, and recovering the GMP adsorbed onto the resin by elution. This procedure can be carried out either continuously or semicontinuously, for example by extracting saturated resin from the column countercurrentwise and by replacing the saturated resin with freshly regenerated resin.

The term "anion-exchange resin" includes any anion-exchange resin whose matrix is hydrophobic including anion-exchange resins wherein the exchanging groups are weakly basic in macroporous or macrocross-linked. Preferably, the matrix is polystyrene or polyacrylic, gel form, particularly based on polystyrene/divinylbenzene copolymer and more preferably macrocross-linked because of considerations of resistance to osmotic shocks. The weakly basic groups include active groups such as primary to tertiary amines. The resin should be mostly in alkaline form ("OH⁻ form") and therefore the resin's active sites should preferably be generally regenerated in this form.

As used herein the term "lactic raw material" includes any product or by-product containing GMP which can be derived from the milk of ruminants, such as cows, goats, sheep or buffaloes. Lactic raw materials include sweet whey obtained after separation of casein coagulated with rennet a concentrate of sweet whey, a sweet whey or such a whey demineralized to a greater or lesser degree, for example, by electrodialysis, ion exchange, reverse osmosis, electrodeionization or a combination of these procedures, a concentrate of sweet whey demineralized to a greater or lesser degree, for example, by electrodialysis, ion exchange, reverse osmosis, electrodeionization or a combination of these procedures, a concentrate of proteins of substantially lactose-free sweet whey obtained, for example, by ultrafiltration, followed by diafiltration (ultrafiltration with washing), mother liquors of the crystallization of lactose from sweet whey, a permeate of ultrafiltration of a sweet whey, the product of hydrolysis, by a protease, of a native casein obtained by acid precipitation of skimmed milk with an inorganic acid or by biological acidification, where appropriate with addition of calcium ions or alternatively of a micellar casein, obtained for example by microfiltration of a skimmed milk, the product of hydrolysis of a caseinate by a protease.

Preferably the lactic raw material includes a preconcentrated sweet whey from cheesemaking, a protein concentrate of lactose-free and cation-free sweet whey, more preferably, preconcentrated sweet whey from cheesemaking at 10–23% by weight and decationized or completely deionized, i.e., substantially free of cations and anions.

The lactic raw materials may be provided in liquid or in powdered form. In the latter case, the powders are dispersed in water, preferably demineralized to be subsequently treated.

During the step of bringing into contact the liquid raw materials with the weakly basic anionic matrix, the active sites of the resin are exchanged against the GMP molecules, producing a gradual increase in the pH of the treated liquid material. The pH may increase up to a stabilized final value, such as a pH range of between about 4.5 to about 5.5 depending on the raw material used. The duration of the operation and the amount of resin and treated liquid are chosen as a function of the composition of the starting material and the desired quantity of GMP.

The duration of the process of the present invention may last from between about 1 h to about 10 h, preferably about 4 h. The respective proportions of resin and liquid to be treated can vary widely depending on the desired degree of separation of the GMP. One of ordinary skill in the art with little or no experimentation can determine the desired proportions of resin and lactic raw material to be treated. Preferably, the proportions include a ratio of between about 1:1 to about 1:30 and more preferably from between about 1:1 to about 1:10 by volume.

Optionally, the treated liquid can be concentrated and, if desired, dried. The treated liquid can be concentrated by evaporation and consequently dried by spray-drying in a drying tower. The treated liquid obtained from the process of the present invention has an amino acid profile which is reduced in threonine and enriched in aromatic amino acids land tryptophan. Preferably, the treated liquid obtained has a threonine content reduced by about 15% to about 40% and the aromatic amino acids and tryptophan content are increased to about 20% to about 60% relative to the lactic raw material. This treated liquid material is useful in an infant or dietetic product as a protein raw material, in a pharmaceutical composition in combination with antithrombotic, antidiarrheal or antibacterial agents, or in a food composition as an emulsifying, gelling or foaming agent.

The processes of the present invention can be conducted in a reactor, a column, or a combination thereof. The combination can be carried out using a device whose upper part is a reactor provided with means for stirring or for producing a fluidized bed containing the resin, separated by a grid or a filter from a lower part. The lower part includes a column wherein the resin can be recovered at the end of the treatment, such as by decantation, and the treated liquid material can be drawn off.

Separating the GMP from the resin typically comprises first treating the resin by washing the resin with demineralized water to obtain an eluate. Optionally, the resin may be washed with a dilute saline solution or a dilute acidic solution and rinsed with demineralized water. Desorption of the GMP is accomplished by washing the resin with an aqueous solution of acid, base or salt, preferably by washing the resin with a basic aqueous solution, followed by washing with demineralized water. Basic aqueous solutions include but are not limited to solutions of NaOH, KOH or Ca(OH)$_2$ with a concentration of about less than 8% by weight, preferably with a concentration of between about 0.5 to about 3%. This process advantageously regenerates the resin at the same time GMP desorption occurs. Subsequently, the eluate and washings are combined and demineralized by ultrafiltration or nano-filtration on a membrane with a mean cut-off region of about 3000 daltons to obtain a retentate and a filtrate. The retentate is dried, preferably by freeze-drying. Even after up to 150 treatment cycles, there is no decrease in the performance of the resin or fouling thereof.

The GMP obtained is substantially free of fat and of lactose and is low in whey proteins. Preferably, the GMP obtained using the process of the present invention contains <1% fat, <0.2% of lactose, and <3% of true whey proteins, by weight.

The GMP obtained by the process of the present invention can be used in applications including pharmaceutical compositions such as antithrombotic, antidiarrheal or antibacterial agents administered in oral, parenteral or subcutaneous formulations, dental hygiene compositions such as an agent against plaque and caries or alternatively in foods, such as confectionery products for its properties against plaque and against caries. The GMP may also be used either for its functional properties such as an emulsifying agent, gelling agent or foaming agent or for its dietetic properties, such as in antiphenylketonuria infant compositions because it does not contain phenylalanine.

The drawing illustrates preferred devices for use in the process of the present invention. A reactor 1 has in its upper section a principal tank 2 connected to a lower part having a compartment 3 through a smaller diameter than that of the tank 2. Tank 2 has a rinsing liquid inlet channel 4, an inlet 5 to allow entry of pressurized gas, a safety valve 6 to regulate the gas pressure in reactor 1. Close to the base of tank 2 there is a strainer 7 and a channel 8 for drawing off liquid.

Connected to compartment 3, the reactor has a pH-meter 9, a gas inlet 10 and a three-way valve 11 connected to an inlet channel 12 for liquid to be treated and a discharge channel 13 to remove treated liquid. The base of compartment 3 has a grid or a perforated plate 14 which collects resin beads 15. Under grid 14, a drawing-off channel 16 removes the liquid via pump 17 to a buffer tank 18, which has a level controlling device 19. Channel 20 via pump 21 removes liquid from buffer tank 18. Channel 20 is connected either to the channel 12, or to the discharge overflow 22.

EXAMPLES

The examples below illustrate the invention, as well as FIG. 1 of the drawing, showing, schematically and with no limitation being implied, a preferred device for carrying out the invention. In the examples, the parts and percentages are by weight unless otherwise stated.

Example 1

A bovine sweet whey protein concentrate, conventionally treated by electrodialysis and freed of cation on a strongly cationic resin, was dispersed in deionized water such that the solution had a dry matter content of 6.5%. The concentrate had the composition below:

| Ingredients | Weight % |
| --- | --- |
| Proteins (GMP included) | 76 |
| Lactose | 4.8 |
| Ash | 2.5 |
| Lipids | 8 |
| Water | balance for 100 |

127 kg of the dispersion, of initial pH 4.25 and at a temperature of 12° C., were introduced via channel 12 into reactor 1. Air was introduced by bubbling into compartment 3 through the base by the inlet 10 via a non-return valve 23. A fluidized bed of resin beads 15 was created comprising 23 kg of weakly anionic resin of hydrophobic matrix based on polystyrene (IMAC HP 661®, Rohm & Haas, regenerated in OH$^-$ form). The resin beads 15 were stirred for 4 h in contact with the dispersion due to the turbulence created by the fluidization. The pH of the liquid was constantly controlled by means of the pH-meter 9. Stabilization of the pH at 5.08 indicated the end of the reaction. The air supply at inlet 10 was cut off and air was introduced through inlet 5 at the top of the reactor above the liquid level 24. The liquid was pressurized and the resin beads settled in the lower part of compartment 3 of reactor 2 where they were retained by grid 14. The treated liquid material was drawn off by gravity through channel 8 and through channel 16 by means of pump 17 towards buffer tank 18. The treated liquid material was then discharged by channel 20 by means of pump 21 and directed towards the outlet by channels 12 and 13.

The treated liquid material was concentrated to 28% dry matter by evaporation and the concentrate was spray-dried in a drying tower. Analysis of the concentrate by high-performance liquid chromatography ("HPLC") showed that the reaction removed 91% of the starting GMP. Moreover, the powder contained 95% of the starting whey proteins.

To recover the GMP, the reactor and the resin were washed with deionized water introduced through inlet channel 25, via valve 26, and inlet channel 4 and flushed through the reactor via channels 12 and 13. The GMP was eluted twice through the same circuit with 40 l of aqueous 2% NaOH introduced via channel 27 and valve 28 and rinsed with 30 l of deionized water. After combining the eluate and washing volumes, the volume was concentrated to 25 l by ultrafiltration or nanofiltration with a membrane having a nominal cut-off of 3000 daltons to obtain a retentate and a filtrate. The retentate was freeze-dried and 750 g of GMP were obtained, corresponding to a yield of 82% relative to the starting GMP.

Periodically, the resin was subjected to acidic regeneration after alkaline regeneration once the equivalent of 10 volumes of resin bed had been treated. After elution of the GMP with the alkaline solution as described above, the resin was washed with a concentrated aqueous solution of HCl supplied by channel 29 and valve 30, followed by water supplied by channel 25 and valve 26. The resin was converted to the OH$^-$ form by passing a concentrated aqueous solution of NaOH supplied by channel 27 followed by water from channel 25, into channel 4. The solutions were removed from reactor 1 via channel 16, transferred by pump 17 to the buffer tank 18. From buffer tank 18, the solutions were removed by pump 21, discharged by channel 20 and overflow 22 into the effluent treatment. Following this operation, the resin was ready for another treatment cycle.

Example 2

A bovine sweet whey was used which had been previously concentrated to 17% dry matter, demineralized by electrodialysis, freed of cation on a strongly cationic resin column, freed of anion on a weakly anionic resin column, and spray-dried in a drying tower. The bovine sweet whey had the composition:

| Ingredients | Weight % |
| --- | --- |
| Proteins (GMP included) | 11.7 |
| Lactose | 81.7 |
| Ash | 1 |
| Lipids | 1 |
| Water | balance for 100 |

The demineralized whey powder was solubilized in deionized water. After cation removal the solution had an initial pH of 3.8. Using the plant of example 1, 392 kg of the solution were treated at 8° C., while stirring for 4 h in the reactor in the presence of 23 kg of weakly anionic resin of hydrophobic matrix based on polystyrene (IMAC HP 661®, Rohm & Haas, regenerated in OH⁻ form). Stabilization of the pH at 4.89 indicated the end of the reaction. The treated liquid material was drawn off and the resin was recovered as described above.

After concentration of the treated liquid material to 45% dry matter by evaporation, the concentrate was spray-dried in a drying tower. Analysis of the concentrate by HPLC showed that the reaction removed 89% of the starting GMP. Moreover, the powder contained 9.1% of whey proteins, which corresponded to a yield of 90% of the whey proteins.

To recover the GMP, the resin was washed successively with deionized water, 30 l of an aqueous solution at 0.5% HCl, and 30 l of deionized water. Subsequently, the GMP was eluted twice with 40 l of 2% $Ca(OH)_2$ and rinsed with 30 l of deionized water. After combining the eluate and rinsing volumes, the whole was concentrated to a volume of 25 l by ultrafiltration with a membrane having a nominal cut-off of 3000 daltons to obtain a retentate and a filtrate. The retentate was freeze-dried and 900 g of GMP were obtained which corresponded to a yield of 80% relative to the starting GMP.

Example 3

The starting material was a sweet whey preconcentrated to 18% dry matter, freed of cation by treatment on a column of strongly cationic resin, and having an initial pH of 1.09. 70 kg of the whey were treated at 25° C. while stirring for 4 h in the reactor in the presence of 14 kg of weakly anionic resin of hydrophobic matrix based on polystyrene (IRA 96®, Rohm & Haas, regenerated in OH⁻ form). Stirring was provided by the creation of a fluidized bed of resin beads using bubbling nitrogen. Stabilization of the pH at 4.79 indicated the end of the reaction. The treated liquid material was separated from the resin, concentrated to 45% dry matter by evaporation, and the concentrate was spray-dried in a drying tower.

Analysis of the powder by HPLC showed that the reaction removed 85% of the starting GMP. The powder contained 9.2% of the whey proteins, corresponding to a yield of 90% of the whey proteins. Analysis of the aminogram of the concentrate showed a profile characterized by a 28% decrease in threonine, an 18% increase in arginine, and a 20% increase in tryptophan relative to the lactic raw material.

To recover the GMP, the resin was successively washed with deionized water, 50 l of 0.05% NaCl, and twice with 50 l of deionized water. Subsequently, the GMP was eluted twice with 25 l of 0.6% KOH and rinsed with 10 l of deionized water. The combination of eluate and rinsing volumes was concentrated to a volume of 25 l by ultrafiltration with a membrane having a nominal cut-off of 3000 daltons, and the retentate was freeze-dried. 175 g of GMP were obtained, corresponding to a yield of 80% relative to the starting GMP.

Example 4

A powder of sweet whey ultrafiltration permeate, freed of most of its salts, with the following composition, was used as starting material:

| Ingredients | Weight % |
| --- | --- |
| Proteins (GMF included) | 2.75 |
| Lactose | >90 |
| Ash | 1.5 |
| Water | balance for 100 |

The preceding powder was dissolved in demineralized water such that the solution had a dry matter content of 19.35%. This solution was freed of cation by passage over a column of strong cationic resin (IR 120®, Rohm & Haas) to obtain a substantially deionized lactic raw material containing 18.73% of dry matter with a pH of 2.77.

565 g of the solution and 56.5 g of weakly anionic resin of hydrophobic matrix based on polystyrene (IMAC HP 661®, Rohm & Haas, regenerated in OH⁻ form) were stirred for 3 h at 10° C. until the pH stabilized to a final value of 4.53. The permeate thus treated was then separated from the resin beads by filtration and freeze-dried.

The whey protein permeate contained 1.75% of proteins. Analysis of its aminogram showed a profile characterized by a 20% decrease in threonine and by a 50% increase in tryptophan relative to the lactic raw material.

To recover the GMP, the resin was washed with 1 l of deionized water, the GMP was eluted with 50 mL of aqueous 0.6% NaOH, and rinsed with 20 mL of deionized water. The combined eluate and rinsing volumes were concentrated by ultrafiltration with a membrane having a nominal cut-off of 3000 daltons. The retentate was freeze-dried and 870 mg of GMP were obtained.

Example 5

3.5 L of sweet whey, pre-concentrated to 20% dry matter, freed of cation on a column of strongly cationic resin, and of pH 1.09 was percolated through a column containing 450 mL of weak anionic resin of hydrophobic matrix based on polystyrene (IMAC HP 661®, Rohm & Haas), at the rate of 2 bed volumes/h. The equivalent of 4 bed volumes of treated liquid were recovered, constituting 4 equal fractions with a pH ranging from 6 to 3 and in which the quantity of GMP removed ranged from 50 to 9% (evaluated by HPLC). After combining the 4 fractions, a solution of treated liquid with a pH of 4.5 was obtained in which 25% of the GMP had been removed (as compared to the starting whey material).

To recover the GMP, the procedure of Example 1 was followed with equivalent results with regard to the purity of the GMP.

What is claimed is:

1. A process for obtaining a fraction of a lactic raw material enriched in glycomacropeptide or caseinoglycomacropeptide ("GMP") comprising the steps of:
   deionizing a lactic raw material for a time sufficient to obtain a substantially deionized lactic raw material having a pH of about 1 to 4.5 with the pH being adjusted, if necessary, to the recited range;
   contacting the substantially deionized lactic raw material with an anionic resin having a hydrophobic matrix for a sufficient amount of time and at a sufficient temperature to adsorb a substantial amount of GMP onto the anionic resin from the substantially deionized lactic raw material and to obtain a treated liquid material that does not contain substantial, amounts of GMP;

separating the resin from the treated liquid material; and separating the adsorbed GMP enriched fraction from the resin.

2. The process according to claim 1 wherein the lactic raw material is one of sweet whey obtained after separation of casein coagulated with rennet, a concentrate of sweet whey, a sweet whey or such a whey demineralized to by electrodialysis, ion exchange, reverse osmosis, electrodeionization or a combination of these procedures, a concentrate of sweet whey demineralized by electrodialysis, ion exchange, reverse osmosis, electrodeionization or a combination of these procedures, a concentrate of proteins of substantially lactose-free sweet whey obtained by ultrafiltration, followed by diafiltration (ultrafiltration with washing), mother liquors of the crystallization of lactose from sweet whey, a permeate of ultrafiltration of a sweet whey, the product of hydrolysis, by a protease, of a native casein obtained by acid precipitation of skimmed milk with an inorganic acid or by biological acidification, where appropriate with addition of calcium ions or alternatively of a micellar casein, obtained by microfiltration of a skimmed milk, the product of hydrolysis of a caseinate by a protease.

3. The process according to claim 1 wherein the lactic raw material is sweet whey having a solids content of about 10 to 23 percent by weight.

4. The process according to claim 1 wherein the lactic raw material is a liquid or a dispersion of solids in a liquid.

5. A process for obtaining a fraction of lactic raw material enriched in glycomacropeptide or caseinoglycomacropeptide ("GMP") comprising the steps of:

deionizing a lactic raw material for a time sufficient to obtain a substantially deionized lactic raw material having a pH of about 1 to 4.5 with the pH being adjusted, if necessary, to the recited range;

contacting the substantially deionized lactic raw material with an anionic resin having a hydrophobic matrix for a sufficient amount of time and at a sufficient temperature to remove GMP from the substantially deionized lactic raw material and to obtain a treated liquid material, wherein the substantially deionized lactic raw material contacts the resin in a gently stirred reactor at a temperature of less than 50° C. for one to ten hours to adsorb the: GMP onto the resin;

separating the resin from the treated liquid material; and separating the GMP enriched fraction from the resin.

6. The process according to claim 5 wherein the reactor is at a temperature between 0° C. and 15° C. and the resin is basic and in macroporous or macrocross-linked gel form.

7. The process according to claim 1 wherein the substantially deionized lactic raw material contacts the resin until the treated liquid material attains a constant pH of about 4.5 to 5.5.

8. A process for the extraction and removal of glycomacropeptide or caseinoglycomacropeptide ("GMP") from a lactic raw material comprising the steps of:

deionizing a lactic raw material for a time sufficient to obtain a substantially deionized lactic raw material having a pH of about 1 to 4.5 with the pH being adjusted, if necessary, to the recited range;

contacting the substantially deionized lactic raw material with an anionic resin having a hydrophobic matrix for a sufficient amount of time and at a sufficient temperature to remove GMP from the substantially deionized lactic raw material by adsorbing a substantial amount of GMP onto the anionic resin to obtain a treated liquid material that does not contain substantial amounts of GMP;

separating the resin from the treated liquid material;

concentrating the treated liquid material by evaporation and drying; and recovering GMP by desorbing it from the resin.

9. The process according to claim 8 wherein the step of separating the resin from the treated liquid material is accomplished by filtration or centrifugation and the treated liquid material is dried by spray drying.

10. The process according to claim 1 wherein the anionic resin and the deionized lactic raw material are present in a ratio by volume of between 1:1 and 1:30.

11. The process according to claim 1, wherein the step of separating the adsorbed GMP enriched fraction from the resin is accomplished by:

washing the resin with demineralized water to obtain a wash;

desorbing the GMP from the resin by washing the resin with an acidic, basic or saline aqueous solution rinse to obtain an eluate;

rinsing the resin with demineralized water to obtain a rinse;

combining the eluate, the rinse and the wash;

demineralizing the combined eluate, rinse and wash by ultrafiltration or nanofiltration on a membrane with a mean cut-off region of about 3000 daltons to obtain a retentate and filtrate; and recovering the GMP enriched fraction as the retentate; and optionally freeze-drying the recovered retentate.

12. The process according to claim 11 wherein the basic aqueous solution comprises NaOH, KOH or $Ca(OH)_2$, in a concentration of less than 8%.

13. A process for obtaining a fraction of a lactic raw material enriched in glycomacropeptide or caseinoglycomacropeptide ("GMP") comprising the steps of:

deionizing a lactic raw material for a time sufficient to obtain a substantially deionized lactic raw material having a pH of about 1 to 4.5 with the pH being adjusted, if necessary, to the recited range;

treating the resin with an alkaline material;

contacting the substantially deionized lactic raw material with an anionic resin having a hydrophobic matrix for a sufficient amount of time and at a sufficient temperature to adsorb a substantial amount of GMP onto the anionic resin from the substantially deionized lactic raw material and to obtain a treated liquid material that does not contain substantial amounts of GMP;

separating the resin from the treated liquid material; and separating the adsorbed GMP enriched fraction from the resin.

14. A process for preparing a composition that contains glycomacropeptide or caseinoglycomacropeptide ("GMP") in combination with a pharmaceutically acceptable carrier, said process comprising the steps of:

(a) deionizing a lactic raw material for a time sufficient to obtain a substantially deionized lactic raw material having a pH of about 1 to 4.5 with the pH being adjusted, if necessary, to the recited range;

(b) contacting the substantially deionized lactic raw material with an anionic resin having a hydrophobic matrix for a sufficient amount of time and at a sufficient temperature to adsorb a substantial amount of GMP onto the anionic resin from the substantially deionized lactic raw material and to obtain a treated liquid material that does not contain substantial amounts of GMP;

(c) separating the resin from the treated liquid material;

(d) separating the adsorbed GMP enriched fraction from the resin; and (e) combining the GMP of step (d) with a pharmaceutically acceptable carrier.

15. The process of claim 14, wherein the composition is an antithrombotic pharmaceutical composition containing GMP as an antithrombotic agent.

16. A process for obtaining a composition comprising a carrier and a fraction of a lactic raw material enriched in glycomacropeptide or caseinoglycomacropeptide ("GMP"), wherein said process comprises the steps of:

deionizing a lactic raw material for a time sufficient to obtain a substantially deionized lactic raw material having a pH of about 1 to 4.5 with the pH being adjusted, if necessary, to the recited range;

contacting the substantially deionized lactic raw material with an anionic resin having a hydrophobic matrix for a sufficient amount of time and at a sufficient temperature to adsorb a substantial amount of GMP onto the anionic resin from the substantially deionized lactic raw material and to obtain a treated liquid material that does not contain substantial amounts of GMP;

separating the resin from the treated liquid material;

separating the adsorbed GMP enriched fraction from the resin; and combining said GMP enriched fraction with a carrier;

wherein said process the GMP enriched fraction includes less than 1% by weight of fat, less than 0.2% by weight of lactose, and less than 3% by weight of true whey products.

* * * * *

UNITED STATES PATENT AND TRADEMARK OFFICE
CERTIFICATE OF CORRECTION

PATENT NO. : 6,787,158 B1
DATED : September 7, 2004
INVENTOR(S) : Erdmann et al.

It is certified that error appears in the above-identified patent and that said Letters Patent is hereby corrected as shown below:

Title page, Item [54] and Column 1, line 1,
Title, change to -- PROCESS FOR THE TREATMENT OF A LACTIC RAW MATERIAL --.

Column 9,
Line 5, after "does not contain substantial", delete ",".
Line 47, after "to adsorb the", delete ":".

Column 12,
Line 17, please add the following claims:
-- 17. The process of claim 1 wherein the treated liquid material has an amino acid profile that is reduced in the threonine and enriched in aromatic amino acids and tryptophan relative to the lactic raw material.
18. The process of claim 17 wherein, relative to the lactic raw material, the threonine content is reduced by about 15 to 40%, and the aromatic amino acids and tryptophan are increased by about 20 to 60%.
19. The process of claim 17, wherein the treated liquid material is included in an infant or dietetic product as protein raw material.
20. The process of claim 9 wherein the treated liquid material is included in an infant or dietetic products as protein raw material.
21. The process of claim 10 wherein the dried treated liquid material is included in an infant or dietetic product as protein raw material.
22. The process of claim 16 wherein the composition is a food composition containing the GMP as an emulsifying, gelling or foaming agent.
23. The process of claim 16 wherein the composition is a dental composition containing the GMP as an agent against plaque and caries. --
24. The process according to claim 12, further comprising the step of freeze-drying the retentate. --

Signed and Sealed this

Eighteenth Day of January, 2005

JON W. DUDAS
*Director of the United States Patent and Trademark Office*